(12) United States Patent
Kim et al.

(10) Patent No.: US 9,220,704 B2
(45) Date of Patent: Dec. 29, 2015

(54) COMPOSITE FORMULATION COMPRISING A TABLET ENCAPSULATED IN A HARD CAPSULE

(71) Applicant: HANMI PHARM CO., LTD., Hwaseong-si, Gyeonggi-do (KR)

(72) Inventors: Kyeong Soo Kim, Suwon-si (KR); Ki Young Jang, Suwon-si (KR); Seung Jae Park, Seoul (KR); Yong Il Kim, Suwon-si (KR); Jae Hyun Park, Suwon-si (KR); Jong Soo Woo, Suwon-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 14/345,983

(22) PCT Filed: Oct. 15, 2012

(86) PCT No.: PCT/KR2012/008380
§ 371 (c)(1),
(2) Date: Mar. 20, 2014

(87) PCT Pub. No.: WO2013/055177
PCT Pub. Date: Apr. 18, 2013

(65) Prior Publication Data
US 2014/0227356 A1 Aug. 14, 2014

(30) Foreign Application Priority Data

Oct. 13, 2011 (KR) .................. 10-2011-0104374

(51) Int. Cl.
*A61K 31/24* (2006.01)
*A61K 9/20* (2006.01)
(Continued)

(52) U.S. Cl.
CPC ............. *A61K 31/24* (2013.01); *A61K 9/205* (2013.01); *A61K 9/2086* (2013.01);
(Continued)

(58) Field of Classification Search
CPC ............ A61K 31/4178; A61K 31/616; A61K 31/549; A61K 31/4422; A61K 31/5415; A61K 31/24; A61K 31/40; A61K 31/4453; A61K 31/47; A61K 31/495; A61K 9/205; A61K 9/2086; A61K 9/2866; A61K 2300/00
USPC .......... 424/454; 514/161, 224.2, 255.04, 317, 514/356

See application file for complete search history.

(56) References Cited

U.S. PATENT DOCUMENTS

| 4,851,230 A | 7/1989 | Tencza et al. |
| 5,089,270 A | 2/1992 | Hampton et al. |

(Continued)

FOREIGN PATENT DOCUMENTS

| EP | 0435726 A2 | 7/1991 |
| GB | 1 204 580 | * 9/1970 |
| GB | 1204580 A | 9/1970 |

OTHER PUBLICATIONS

European Patent Office, Communication dated Mar. 2, 2015 issued in corresponding European application No. 12840479.5.
(Continued)

*Primary Examiner* — Blessing M Fubara
(74) *Attorney, Agent, or Firm* — Sughrue Mion, PLLC (57) ABSTRACT

The present invention relates to a hard capsule composite formulation comprising a capsule having a hemispherical closure at each end and an interior space; and one or more tablets encapsulated in the capsule, wherein the tablet or the tablets as a whole have a shape conforming to the internal space of the capsule. The hard capsule composite formulation can efficiently charge pharmaceutical compositions inside the limited interior space of the capsule, and hence, it allows packing a high-dose of pharmaceutical composition in a relatively small-sized capsule, which increases productivity and patient compliance. Also, the composite formulation exhibits good dissolution rate because pharmaceutically active ingredients contained in the capsule are separated from one another, and thus, the ingredients are less affected by the dissolution rate of one another, allowing good storage stability which can optimize the therapeutic effects.

11 Claims, 4 Drawing Sheets

(51) Int. Cl.
    *A61K 9/28*      (2006.01)
    *A61K 31/4178*   (2006.01)
    *A61K 31/4422*   (2006.01)
    *A61K 31/549*    (2006.01)
    *A61K 31/40*     (2006.01)
    *A61K 31/4418*   (2006.01)
    *A61K 31/4453*   (2006.01)
    *A61K 31/47*     (2006.01)
    *A61K 31/495*    (2006.01)
    *A61K 31/5415*   (2006.01)
    *A61K 31/616*    (2006.01)
    *A61K 9/48*      (2006.01)

(52) U.S. Cl.
    CPC ............ *A61K 9/2866* (2013.01); *A61K 9/4808* (2013.01); *A61K 31/40* (2013.01); *A61K 31/4178* (2013.01); *A61K 31/4418* (2013.01); *A61K 31/4422* (2013.01); *A61K 31/4453* (2013.01); *A61K 31/47* (2013.01); *A61K 31/495* (2013.01); *A61K 31/549* (2013.01); *A61K 31/5415* (2013.01); *A61K 31/616* (2013.01)

(56) References Cited

U.S. PATENT DOCUMENTS

| | | | |
|---|---|---|---|
| 5,391,381 A | | 2/1995 | Wong et al. |
| 5,456,919 A | | 10/1995 | Patell et al. |
| 5,683,718 A | * | 11/1997 | Errigo ............................ 424/464 |
| 6,245,350 B1 | | 6/2001 | Amey et al. |
| 2003/0170181 A1 | * | 9/2003 | Midha ........................ 424/10.4 |
| 2003/0194428 A1 | | 10/2003 | Miller et al. |
| 2008/0102116 A1 | | 5/2008 | Perry et al. |
| 2009/0291136 A1 | | 11/2009 | Stanic Ljubin et al. |

OTHER PUBLICATIONS

International Searching Authority, International Search Report, PCT/KR2012/008380, dated Feb. 28, 2013.

* cited by examiner

COMPOSITE FORMULATION COMPRISING A TABLET ENCAPSULATED IN A HARD CAPSULE

CROSS REFERENCE TO RELATED APPLICATIONS

This application is a National Stage of International Application No. PCT/KR2012/008380 filed Oct. 15, 2012, claiming priority based on Korean Patent Application No. 10-2011-0104374 filed Oct. 13, 2011, the contents of all of which are incorporated herein by reference in their entirety.

FIELD OF THE INVENTION

The present invention relates to a composite formulation comprising a tablet encapsulated in a hard capsule.

BACKGROUND OF THE INVENTION

The advancement in the field of medicine has improved the quality of life and increased the life expectancy of humans. However, there is a limit to the efficacy of a single pharmaceutically active ingredient in treating patients with medical disorders. Thus, it is common to administer multiple medications having different mechanisms (modes) of action simultaneously or sequentially for synergistic effects. For instance, the risk factors of such a chronic cardiovascular disease as hypertension and the like are well-known, yet most patients are treated with medications due to the difficulties in their risk factor management. It is also difficult to treat them owing to their low compliance to taking medicine. In case where consistent and incessant use of medications seems inevitable, it is advised to use multiple medications having different mechanisms of action so as to provide effective prevention and treatment, as well as to reduce potential undesirable side effects, which may attribute to the long-term use of a single drug. According to the Seventh Report of the Joint National Committee on Prevention, Detection, Evaluation, and Treatment of High Blood Pressure (JNC7), it is recommended to use multiple medications having different mechanisms of action in case where administration of a single drug has failed to effectively control blood pressure.

However, administration of two or more separate drugs may reduce patents' compliance to taking medicine, causing great inconvenience to the patients who are subjected to continuous drug treatments. Further, the patients normally have to carry such separate drugs with them. It will also give the patients great inconvenience in their daily lives.

In order to redress such problems, there has been suggested a method of packaging a number of medications in a single package. For instance, Torrent Pharmaceuticals Ltd. (India) has released a composite formulation "CVpill," a single kit containing a capsule and a tablet for treating a cardiovascular disease. CVpill consists of a capsule containing 10 mg of Atorvastatin in powder form, Ramipril in powder form and 75 mg of an enteric-coated aspirin tablet, and a tablet containing 50 mg of sustained-release Metoprolol. The capsule and the tablet must be administered once a day simultaneously. But such co-packaged products consisting of a simple kit can hardly improve patients' compliance to taking medicine, which, however, may be expected in a composite formulation. Therefore, there is a growing demand for a research on development of a "combination drug or composite formulation" of specific active ingredients.

The term "composite formulation," as used herein, refers to a combination of two or more different active ingredients or drugs in a single unit dose such as tablet or capsule. However, development of a composite formulation for specific active ingredients is sometimes very difficult for the following reasons.

First, the combination of specific active ingredients to be used for a composite formulation should readily be made. Further, the composition comprising active ingredients and a pharmaceutically acceptable excipient should be in appropriate size and weight for administration thereof. However, it is not always easy to develop such composite formulations. If the amount of drugs to be employed is excessive or insufficient, it would be difficult to adjust the weight of the composition to an appropriate level. Also, unexpected problems may be encountered in the course of dealing with the various conditions resulting from the pharmacokinetical and pharmaceutical properties of the drugs.

Second, the chemical interactions between the active ingredients in the preparation of a composite formulation may reduce the stability of drugs. Especially, it is even more difficult to develop a fixed combination dosage form with sufficient physicochemical stability for a combination of drugs if the stability thereof may be reduced due to their chemical interaction when combined.

When a composite formulation of tablet is prepared, a double-layer or a triple-layer tabletting machine can be used to separate the active ingredients. However, not only does such method require special equipments, but it is also mechanically impossible to completely separate the main ingredients in each layer since an undesirable reaction may take place at the interface of the layers.

For a capsule, a conventional hard capsule is charged with drugs in the form of powder, granule or pellet. Conventionally, only a single active ingredient is generally charged in a hard capsule by a single charging step. Also, a drug in the form of powder, granule or pellet has a density lower than that of a tablet since the former is not subjected to a high pressure compressing step. Thus, there exists a limit in the amount of drugs in the form of powder, granule or pellet to be charged in a capsule. In order to charge a high dose of a main ingredient or more than one active ingredient in a single hard capsule, the size of capsule must be increased to accommodate such change. The weight of drugs to be charged in a hard capsule is proportional to the internal volume of the hard capsule, particularly the volume of the capsule body. The internal volume varies with the size of hard capsules: No. 00 (0.95 mL), No. 0 (0.68 mL), No. 1 (0.47 mL), No. 2 (0.37 mL), No. 3 (0.27 mL), and No. 4 (0.20 mL) (see Suheung Capsule homepage). If the size of the capsule becomes too big for accommodating a large amount of drugs, it may cause swallowing difficulties, e.g., dysphagia. Particularly, capsules having large sizes of No. 00 (8.5 mm in capsule cap diameter and 23.3 mm in capsule length) and No. 0 (7.6 mm in capsule cap diameter and 21.7 mm in capsule length) may cause difficulties for elderly people or children to swallow them. It may also be inconvenient to carry them due to their large size.

Therefore, the present inventors have endeavored to resolve the disadvantages of a composite formulation and developed a composite formulation comprising a tablet encapsulated in a hard capsule and having a shape conforming to the capsule body.

SUMMARY OF THE INVENTION

It is an object of the present invention to provide a composite formulation with good storage stability and a dissolution rate, which is in an appropriate size for administration with a high charge rate in a capsule.

In accordance with one object of the present invention, there is provided a hard capsule composite formulation comprising a capsule having a hemispherical closure at each end and an internal space; and a tablet placed in the capsule, wherein the tablet has a shape conforming to the internal space of the capsule.

The inventive hard capsule composite formulation can efficiently charge pharmaceutical compositions in the limited internal space of the capsule. Hence, it is possible to charge a high dose of a pharmaceutical composition in a relatively small-sized capsule, to thereby increase the productivity and render it readily administered to patients. The capsule has a good dissolution rate because the pharmaceutically active ingredients contained in the capsule are separated from one another; therefore, the dissolution rates of the ingredients are less affected by one another. It may also be possible to maximize the therapeutic effects of the pharmaceutically active ingredients since the composite formulation has good stability.

Other features and embodiments of the present invention will be apparent from the following description and the appended claims.

BRIEF DESCRIPTION OF DRAWINGS

The above and other objects and features of the present invention will become apparent from the following description of the invention, when taken in conjunction with the accompanying drawings, in which.

DETAILED DESCRIPTION OF THE INVENTION

Embodiments of the present invention are explained in detail hereinafter.

In a specific embodiment, the present invention provides a hard capsule composite formulation comprising a capsule having a hemispherical closure at each end and an internal space; and a tablet placed in the capsule, wherein the tablet has a shape conforming to the internal space of the capsule.

Figure 1:
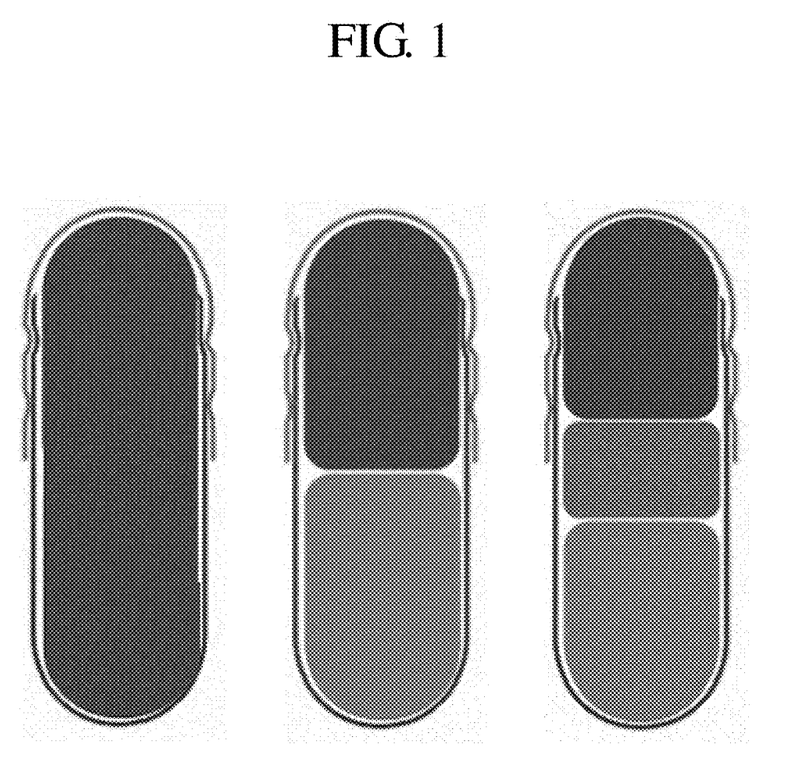
FIG. 1 shows a schematic view of a hard capsule composite formulation in accordance with Examples 1 and 2 of the present invention.

The schematic view of the first embodiment of the hard capsule composite formulation is shown in the left side of FIG. 1. The hard capsule composite formulation has a capsule and a tablet. The capsule may be any conventional capsule used in the pharmaceutical industry. It has a hemispherical closure at each end and an internal space. In a conventional capsule, the internal space is usually charged with powders, granules, or pellets. However, the inventive composite formulation is charged with a tablet having a shape conforming to the internal space of the capsule.

In another specific embodiment, the present invention provides a hard capsule composite formulation comprising a first tablet and a second tablet, wherein the first tablet and the second tablet each have a cylindrical body with a hemispherical end and a flat end, and the tablets are positioned in the capsule with their flat ends facing each other.

The schematic view of the second embodiment of the hard capsule composite formulation is shown in the middle of FIG. 1. The hard capsule composite formulation has a capsule and two tablets. The capsule may be any conventional capsule used in the pharmaceutical industry. It has a hemispherical closure at each end and an internal space. In a conventional capsule, the internal space is usually charged with powders, granules, or pellets. However, the composite formulation is charged with two tablets having a shape conforming to a half of the internal space of the capsule. The tablets are separately prepared and are charged in the internal space of the capsule with their flat ends facing each other.

In another specific embodiment, the present invention provides a hard capsule composite formulation comprising a first tablet, a second tablet, and a third tablet, wherein the first tablet and the second tablet each have a cylindrical body with a hemispherical end and a flat end, and the third tablet has a cylindrical body with two flat ends and is positioned in between the first tablet and the second tablet with their flat ends facing each other.

The schematic view of the third embodiment of the hard capsule composite formulation is shown in the right side of FIG. 1. The hard capsule composite formulation has a capsule and three tablets. The capsule may be any conventional capsule used in the pharmaceutical industry. It has a hemispherical closure at each end and an internal space. In a conventional capsule, the internal space is usually charged with powders, granules, or pellets. However, the composite formulation is charged with three tablets, wherein the first tablet has a cylindrical body with a hemispherical end, which conforms to the hemispherical end of the internal space of the capsule, and a flat end; the second tablet has a cylindrical body with two flat ends; and the third tablet has a cylindrical body with a hemispherical end and a flat end like the first one.

In the inventive composite formulation, the tablet can be prepared by subjecting a mixture or granules of pharmacologically active ingredients and pharmaceutically acceptable excipients to a compression step with a tabletting machine. In such case, the hardness of the tablet is determined by the magnitude of the compression pressure. When the hardness of a tablet changes, so does the density of the tablet, even if the compositions are the same. Typically, the tablet has a density of 0.8 g/mL or greater. The tablet can be prepared in the form of cylinder, rectangle, or oval. In case where tablets having said shape are charged in the internal space of a capsule, a sufficient amount of tablets for producing a desired pharmaceutical effect may not be charged due to excessive voids to be formed between the tablets in the capsule, although the tablets themselves have relatively high densities. In contrast, since the tablet in accordance with the present invention has a shape conforming to the internal space of a capsule, i.e., a bullet shape, it can completely fill in the internal space of the hard capsule without forming any voids in the capsule. Therefore, a larger amount of a pharmaceutical composition can be charged even in a smaller capsule.

In the inventive composite formulation, the diameter of the bullet-shaped tablet should be smaller than the internal diameter of the hard capsule in which the tablet will be charged. If the diameter of the bullet-shaped tablet is larger than the internal diameter of the hard capsule, then the capsule cannot be charged in the capsule. Also, if the diameter of the bullet-shaped tablet is too smaller than the internal diameter of the hard capsule, then the void to be formed between the tablet and the capsule would be too large, thereby impairing the charge rate of the capsule. Therefore, the diameter of the bullet-shaped tablet is preferably adjusted in the range of 0.5 to 0.95 times of the internal diameter of the hard capsule body.

Further, in the inventive composite formulation, the ratio of the radius of the hemispherical ends of the capsule to the radius of the hemispherical ends of the tablet is 1:0.8 to 1:0.99. If the radius of the hemispherical ends of the tablet is smaller than the radius of the hemispherical ends of the capsule by more than 20%, the charge rate of the capsule would not be satisfactory.

In the inventive composite formulation comprising a capsule and two tablets, the two flat ends of the tablets may be slightly curved, rather than completely flat. In such case, the radius of each slightly curved end is twice or more times of the radius of the hemispherical ends of the tablet so as to minimize the void to be formed in the capsule.

Figure 2:
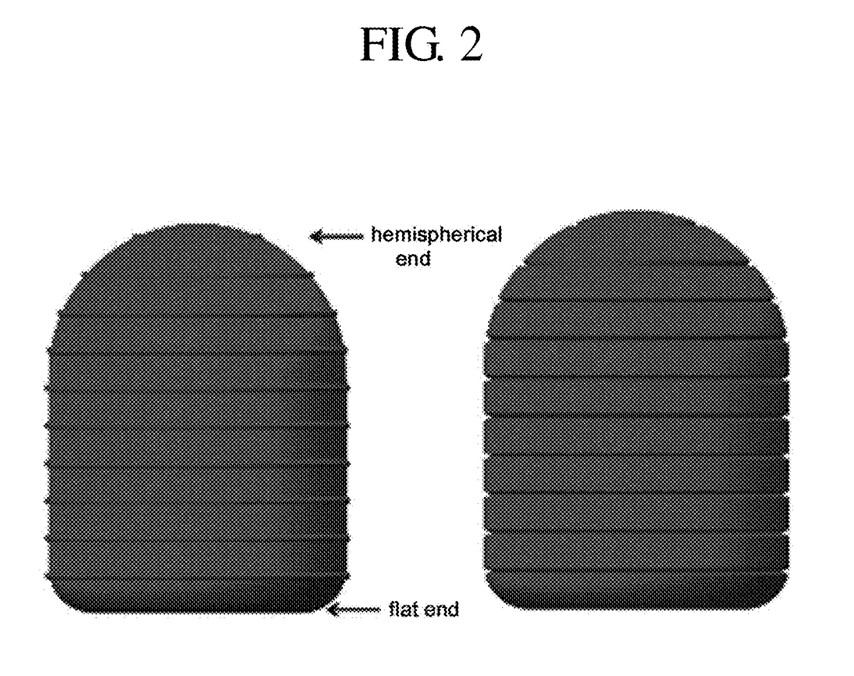
FIG. 2 shows a schematic view of a tablet having horizontal stripes according to one embodiment of present invention, which will be charged in a hard capsule.
Figure 3:
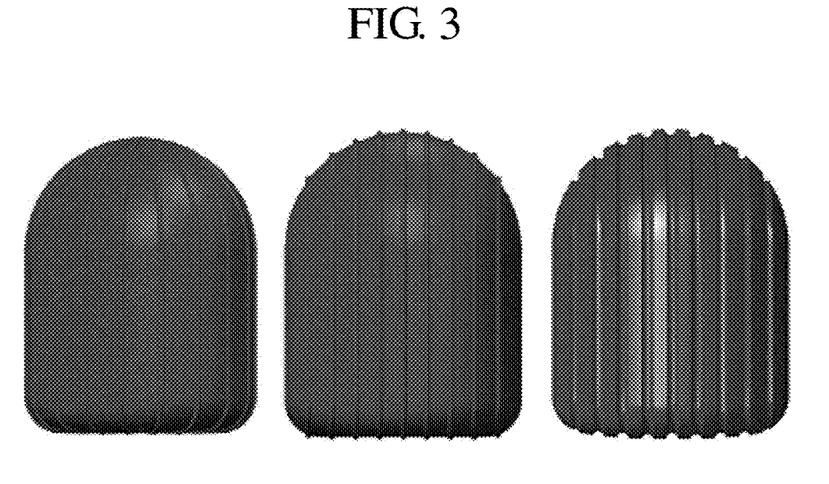
FIG. 3 shows a schematic view of a tablet having vertical stripes according to one embodiment of present invention, which will be charged in a hard capsule.
Figure 4:
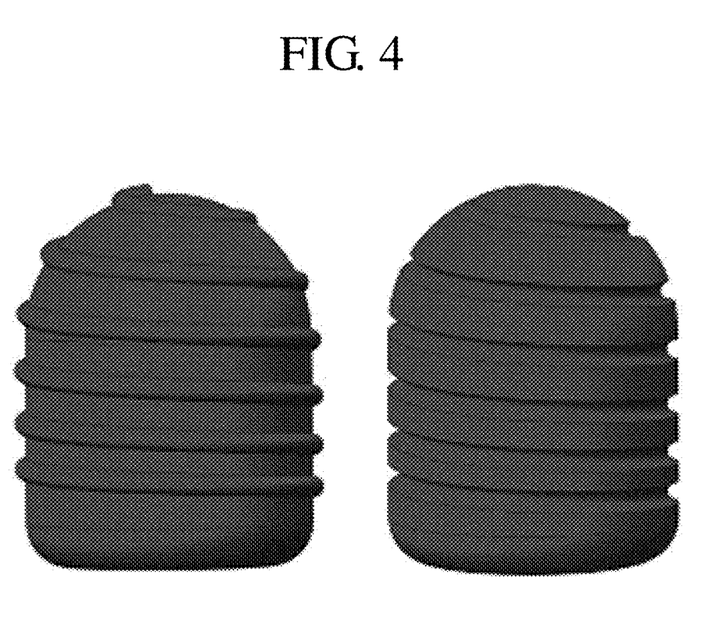
FIG. 4 shows a schematic view of a tablet having oblique stripes according to one embodiment of present invention, which will be charged in a hard capsule.

Further, in one specific embodiment of the inventive composite formulation, the tablet may have stripes of horizontal, vertical or spiral pattern (see FIGS. 2 to 4). FIGS. 2 to 4 illustrate examples of tablets having such patterns; however, the patterns are not limited to the stripes as described above as long as it serves to sustain the release of the active ingredients contained the hard capsule. Various modifications thereof also fall within the scope of the present invention.

The inventive composite formulation demonstrates an enhanced charge rate as compared to conventional granule or pellet type hard capsules. In one embodiment, the rate of material charged in the inventive composite formulation is 0.6 g/mL to 1.0 g/mL. In another embodiment, the charge rate in the inventive composite formulation is 0.7 g/mL to 0.9 g/mL.

The charge rate of a capsule can be calculated by the weight of material charged in the capsule over the volume of the capsule body. For example, when 150 mg of a composition is charged in a No. 2 capsule (vol.: 0.37 mL), the charge rate is approximately 0.41 g/mL. Generally, it is difficult to achieve a charge rate of 0.6 g/mL or greater if granule or pellet material is charged due to the low density of the material charged or the voids existing in the pellet.

In contrast, the composite formulation according to the present invention has a charge rate of 0.6 g/mL or greater, which make it possible to reduce the size of a hard capsule, rendering it readily administered to patients.

Further, the porosity (the rate of empty space) of the interior of the inventive capsule composite formulation is 20% or less. Considering the fact that a conventional granule or pellet type hard capsule normally has a porosity of 25% or greater, the inventive composite formulation has the advantage of being capable of reducing its porosity.

In the inventive composite formulation, the tablet may comprise pharmaceutically acceptable diluents as an additive in addition to the active ingredients. Examples of diluents include microcrystalline cellulose, lactose, ludipress, mannitol, monocalcium phosphate, starch, low-substituted hydroxypropyl cellulose, and a mixture thereof. The amount of diluents employed may be, based on the total weight of the composition, about 1 to 99%, preferably about 5 to 95%. Further, the tablet in accordance with the present invention may further comprise pharmaceutically acceptable additives, e.g., disintegrants, binders, stabilizers, lubricants, colorants, and the like. The disintegrants in the present invention include any material that safely swells in a liquid environment, which is selected from the group consisting of crospovidone, sodium starch glycolate, croscarmellose sodium, low-substituted hydroxypropyl cellulose, starch, alginate or its sodium salt, or a mixture thereof. In one embodiment, the disintegrants are low-substituted hydroxypropyl cellulose, crospovidone, sodium starch glycolate, croscarmellose sodium, or a mixture thereof. The amount of disintegrants employed may be, based on the total weight of the tablet, about 1 to 30 wt %, preferably about 2 to 15 wt %. Specific examples of binders that may be employed for the tablet in the present invention include hydroxypropyl cellulose, hydroxypropyl methylcellulose, polyvinyl pyrrolidone, copovidone, macrogol, light anhydrous silicic acid, synthetic aluminum silicate, silica derivatives such as calcium silicate or magnesium metasilicate aluminate, phosphates such as dicalcium phosphate, carbonates such as calcium carbonate, and a mixture thereof. Examples of stabilizers include antioxidants, acidifying agents, and basifying agents. Specific examples of antioxidants include butylated hydroxytoluene (BHT), butylated hydroxyanisole (BHA), ascorbic acid, ascorbyl palmitate, ethylenediaminetetraacetic acid (EDTA), sodium pyrosulfite, and a mixture thereof; particularly, butylated hydroxytoluene is preferred. Examples of acidifying agents include organic acids such as fumaric acid, citric acid, tartaric acid, succinic acid, lactic acid, malic acid, tosylate, oxalic acid, ascorbic acid, glutamic acid, alginic acid, maleic acid, adipic acid and the like; inorganic acids such as hydrochloric acid, sulfuric acid, nitric acid, phosphoric acid, acetic acid, boric acid and the like, and a mixture thereof, preferably fumaric acid, citric acid, tartaric acid, and phosphoric acid. Examples of basifying agents include arginine, lysine, histidine, meglumine, aluminum magnesium silicate, aluminum magnesium metasilicate, or basic minerals such as $NaHCO_3$, $CaCO_3$, $MgCO_3$, $KH_2PO_4$, $K_2HPO_3$, and tribasic calcium phosphate and the like, preferably $NaHCO_3$, $CaCO_3$, $MgCO_3$ or a mixture thereof. The stabilizer can be selected depending on the nature of the pharmaceutically active ingredients. The amount of stabilizer employed may be 0.01 to 10% based on the selected pharmaceutically active ingredients. Specific examples of lubricants include stearic acid, metal stearates such as calcium stearate and magnesium stearate, talc, colloidal silica, sucrose esters of fatty acids, hydrogenated vegetable oil, high melting point wax, glyceryl fatty acid esters, glycerol dibehenate and a mixture thereof.

The inventive composite formulation comprising two or more tablets in a capsule effectively separates the pharmaceutically active ingredients, securing an improved dissolution rate, and a good stability upon long-term storage. The stability of the composite formulation can be improved even more by coating the tablet. In one specific embodiment, the composite formulation may comprise tablets coated with a polymer film layer so as to physically prevent any possible interaction between two or more active ingredients. Any conventional polymer that can form a film coating may be used. Specific examples include water soluble polymers such as polyvinyl alcohol, hydroxyethyl cellulose, hypromellose, polyvinylpyrrolidone, and the like; and water insoluble polymers such as hypromellose phthalate, polyvinyl acetate (e.g., Kollicoat® SR 30D), water insoluble polymethacrylate copolymer [such as, poly(ethyl acrylate-methyl methacrylate) copolymer (e.g., Eudragit® NE30D), poly(ethyl acrylate-methyl methacrylate-trimethylaminoethyl methacrylate chloride) copolymer (e.g., Eudragit® RSPO), and the like], ethyl cellulose, cellulose ester, cellulose ether, cellulose acylate, cellulose diacylate, cellulose triacylate, cellulose acetate, cellulose diacetate, cellulose triacetate, and a mixture thereof, but not limited thereto. The amount of polymer may be adjusted in order to provide a tablet having an appropriate size in an efficient manner, which is preferably about 1 to 20 wt %, more preferably about 1 to 10 wt %, based on the total weight of the tablet. Each tablet is completely separated and forms an independent dosage form, preventing any interaction between the tablets. Also, in the analysis of the stability of active ingredients prepared in accordance with the present invention, it would be sufficient to analyze the stability of each tablet contained in a capsule by a conventional method for analyzing a single medicine, instead of any special method therefor.

Further, in one aspect, the present invention provides a method for preparing a hard capsule composite formulation, which comprises the steps of:

(i) preparing a tablet having a shape conforming to the internal space of a capsule; and (ii) charging the tablet prepared in step (i) into the internal space of the capsule.

In another aspect, the present invention provides a method for preparing a hard capsule composite formulation, which comprises the steps of:

(i) preparing a first tablet and a second tablet, wherein the first tablet and the second tablet each have a cylindrical body with a hemispherical end and a flat end; and (ii) charging the tablets prepared in step (i) into the internal space of a capsule so that the tablets are positioned in the capsule with their flat ends facing each other.

In still another aspect, the present invention provides a method for preparing a hard capsule composite formulation, which comprises the steps of:

(i) preparing a first tablet, a second tablet, and a third tablet, wherein the first tablet and the second tablet each have a cylindrical body with a hemispherical end and a flat end, and the third tablet has a cylindrical body with two flat ends; and (ii) charging the tablets prepared in step (i) into the internal space of a capsule so that the third tablet is positioned in between the first tablet and the second tablet in the capsule with their flat ends facing one another.

The above methods may further comprise a step of coating each tablet.

EXAMPLES

Hereinafter, the present invention is described more specifically by the following examples, but these are provided only for illustration purposes, and the present invention is not limited thereto.

Example 1

Preparation of Composite Formulation I

| Losartan Layer | |
|---|---|
| Losartan Potassium | 100.0 mg |
| Ludipress ® | 33.0 mg |
| Copovidone ® | 7.4 mg |
| Light anhydrous silicic acid | 2.0 mg |
| Microcrystalline Cellulose | 6.0 mg |
| Magnesium Stearate | 1.6 mg |
| Opadry ® Y-1-7000 | 3.0 mg |
| Distilled Water | (15.0 mg) |
| Amlodipine Layer | |
| Amlodipine Camsylate | 15.68 mg (amlodipine 10 mg) |
| Mannitol | 70.0 mg |
| Microcrystalline Cellulose | 56.92 mg |
| Sodium Starch Glycolate | 2.4 mg |
| Hydroxypropyl Cellulose | 3.0 mg |
| Magnesium Stearate | 2.0 mg |
| Opadry ® (Y-1-7000) | 3.0 mg |
| Distilled Water | (15.0 mg) |

A losartan tablet was prepared by mixing the ingredients listed above for the losartan layer and pressing the resulting mixture into a tablet using a tablet press machine, wherein the diameter of the dye was 5 mm, the radius of curvature of the lower punch was 3.0 mm and the upper punch was flat, followed by coating the resulting tablet with a coating solution prepared by dissolving Opadry® Y-1-7000 in distilled water.

Meanwhile, the ingredients listed above for the amlodipine layer were admixed. Then, an amlodipine tablet was prepared by using the same tablet press machine as that used for preparing the losartan tablet to press the mixture into a tablet, followed by coating the resulting tablet with a coating solution prepared by dissolving Opadry® Y-1-7000 in distilled water.

The two tablets were charged in the capsule body of a No. 2 hard capsule (vol. of body: 0.37 mL). The losartan tablet was first charged in the capsule body with its curved-end facing down, and the amlodipine tablet was then charged therein with its curved-end facing up. Subsequently, the capsule body was closed with a capsule cap to produce a composite formulation comprising 100 mg of losartan (total weight of the tablet: 153 mg) and 10 mg of amlodipine (total weight of the tablet: 153 mg). The rate of the composition charged in the capsule body to the volume of the capsule body was satisfactorily about 0.83 g/mL.

Example 2

Preparation of Composite Formulation II

| Losartan Layer | |
|---|---|
| Losartan Potassium | 50.0 mg |
| Ludipress ® | 41.5 mg |
| Copovidone | 3.7 mg |
| Light anhydrous silicic acid | 1.0 mg |
| Microcrystalline Cellulose | 3.0 mg |
| Magnesium Stearate | 0.8 mg |
| Opadry ® Y-1-7000 | 2.0 mg |
| Distilled Water | (10.0 mg) |
| Amlodipine Layer | |
| Amlodipine Camsylate | 15.68 mg (amlodipine 10 mg) |
| Mannitol | 40.0 mg |
| Microcrystalline Cellulose | 36.92 mg |
| Sodium Starch Glycolate | 2.4 mg |
| Hydroxypropyl Cellulose | 3.0 mg |
| Magnesium Stearate | 2.0 mg |
| Opadry ® (Y-1-7000) | 2.0 mg |
| Distilled Water | (10.0 mg) |
| Hydrochlorothiazide Layer | |
| Hydrochlorothiazide | 12.5 mg |
| Lactose Hydrate | 40.0 mg |
| Microcrystalline Cellulose | 39.5 mg |
| Sodium Starch Glycolate | 3.0 mg |
| Hydroxypropyl Cellulose | 3.0 mg |
| Magnesium Stearate | 2.0 mg |
| Opadry ® (Y-1-7000) | 2.0 mg |
| Distilled Water | (10.0 mg) |

A losartan tablet was prepared by mixing the ingredients listed above for the losartan layer and pressing the resulting mixture into a tablet using a tablet press machine, wherein the diameter of the dye was 5 mm, the radius of curvature of the lower punch was 3.0 mm and the upper punch was flat, followed by coating the resulting tablet with a coating solution prepared by dissolving Opadry® Y-1-7000 in distilled water.

Meanwhile, the ingredients listed above for the amlodipine layer above were admixed. Then, the same tablet press machine as that used for preparing the losartan tablet was used to press the mixture into a tablet, followed by coating the resulting tablet with a coating solution prepared by dissolving Opadry® Y-1-7000 in distilled water to yield an amlodipine tablet.

Also, the ingredients of the hydrochlorothiazide layer above were admixed. Then, the resulting mixture was tabletted using a tablet press machine, wherein the diameter of the dye was 5 mm, and both upper and lower punches were flat, followed by coating the resulting tablet with a coating solution prepared by dissolving Opadry® Y-1-7000 in distilled water to yield a hydrochlorothiazide tablet.

The three tablets were charged in the capsule body of a No. 2 hard capsule (vol. of body: 0.37 mL). Specifically, the losartan tablet was first charged in the capsule body with its curved-end facing down, followed by charge of the hydrochlorothiazide tablet, and the amlodipine tablet was then charged therein with its curved-end facing up. Subsequently, the capsule body was closed with a capsule cap to produce a composite formulation comprising 50 mg of losartan (total weight of the tablet: 102 mg), 10 mg of amlodipine (total weight of the tablet: 102 mg), and 12.5 mg of hydrochlorothiazide (total weight of the tablet: 102 mg). The rate of the composition charged in the capsule body to the volume thereof was satisfactorily about 0.83 g/mL.

Example 3

Preparation of Composite Formulation III

| Atorvastatin Layer | |
|---|---|
| Atorvastatin Calcium | 10.36 mg (Atorvastatin, 10 mg) |
| Magnesium Carbonate | 60.0 mg |
| D-Mannitol | 22.79 mg |
| Croscarmellose Sodium | 8.0 mg |
| Microcrystalline Cellulose | 8.0 mg |
| Hydroxypropyl Cellulose | 5.0 mg |
| Tween ® 80 | 0.6 mg |
| Distilled Water | (250.0 mg) |
| Crosscarmellose Sodium | 4.0 mg |
| Magnesium Stearate | 1.25 mg |
| Opadry ® Y-1-7000 | 3.0 mg |
| Distilled Water | (15.0 mg) |
| Aspirin Layer | |
| Aspirin | 100.0 mg |
| Microcrystalline Cellulose | 26.0 mg |
| Pregelatinized Starch | 13.0 mg |
| Light anhydrous silicic acid | 1.5 mg |
| Stearic Acid | 0.5 mg |
| Hypromellose Phthalate | 17.0 mg |
| Titanium Dioxide | 1.7 mg |
| Acetylated Monoglyceride | 0.3 mg |
| Ethanol | (90.0 mg) |
| Distilled Water | (180.0 mg) |

Atorvastatin, magnesium carbonate, D-mannitol, croscarmellose sodium and microcrystalline cellulose among the ingredients listed above for the atorvastatin layer were admixed. Separately, hydroxypropyl cellulose and Tween 80 were dissolved in distilled water. The resulting solution, as a binding solution, was combined with the mixture to form granules by using a fluid bed granulator (Glatt). The resulting granules were mixed with croscarmellose sodium and magnesium stearate; then, the resulting mixture was tabletted using a tablet press machine, wherein the diameter of the dye was 5 mm, the radius of curvature of the lower punch was 3.0 mm and the upper punch was flat, followed by coating the resulting tablet with a coating solution prepared by dissolving Opadry® Y-1-7000 in distilled water to yield an atorvastatin tablet.

Meanwhile, aspirin, microcrystalline cellulose, pregelatinized starch and light anhydrous silicic acid among the ingredients listed above for the aspirin layer were admixed. Stearic acid was added as a lubricant to the resulting mixture, and then the same tablet press machine as that used for preparing the atorvastatin tablet was used to tablet the mixture. Hypromellose phthalate, titanium dioxide, and acetylated monoglyceride were dissolved in a mixed solvent of ethanol and acetone. The resulting solution, as an enteric coating, was coated onto the aspirin tablet to yield a coated aspirin tablet.

The two tablets were charged in the capsule body of a No. 2 hard capsule (vol. of body: 0.37 mL). The aspirin tablet was first charged in the capsule body with its curved-end facing down, and the atorvastatin tablet was then charged therein with its curved-end facing up. Finally, the capsule body was closed with a capsule cap to produce a composite formulation comprising 100 mg of aspirin (total weight of the tablet: 160 mg) and 10 mg of atorvastatin (total weight of the tablet: 123 mg). The rate of the composition charged in the capsule body to the volume thereof was satisfactorily about 0.76 g/mL.

Example 4

Preparation of Composite Formulation IV

| Montelukast Layer | |
|---|---|
| Montelukast Sodium | 10.4 mg (Montelukast, 10 mg) |
| D-Mannitol | 38.15 mg |
| Microcrystalline Cellulose | 32.95 mg |
| Light anhydrous silicic acid | 2.5 mg |
| Sodium Starch Glycolate | 15.0 mg |
| Magnesium Stearate | 1.0 mg |
| Opadry ® II 85F43140 | 2.5 mg |
| Distilled Water | (11.0 mg) |
| Levocetirizine Layer | |
| Levocetirizine Hydrochloride | 5.0 mg |
| Ludipress ® | 60.5 mg |
| Microcrystalline Cellulose | 30.0 mg |
| Croscarmellose Sodium | 3.0 mg |
| Light anhydrous silicic acid | 0.5 mg |
| Magnesium Sterate | 1.0 mg |
| Opadry ® Y-1-7000 | 3.0 mg |
| Distilled Water | (150.0 mg) |

A montelukast tablet was prepared by mixing the ingredients listed above for the losartan layer and pressing the resulting mixture into a tablet using a tablet press machine, wherein the diameter of the dye was 4.5 mm, the radius of the curvature of the lower punch was 3.0 mm and the upper punch was flat, followed by coating the resulting tablet with a coating solution prepared by dissolving Opadry® II 85F43140 in distilled water.

Meanwhile, the ingredients listed above for the levocetirizine layer were admixed. Then, a levocetirizine tablet was prepared by using the same tablet press machine as that used for preparing the montelukast tablet to press the mixture into a tablet, followed by coating the resulting tablet with a coating solution prepared by dissolving Opadry® Y-1-7000 in distilled water.

The two tablets were charged in the capsule body of a No. 3 hard capsule (vol. of body: 0.27 mL). The montelukast tablet was first charged in the capsule body with its curved-end facing down, and the levocetirizine tablet was then charged therein with its curved-end facing up. Subsequently, the capsule body was closed with a capsule cap to produce a composite formulation comprising 10 mg (total weight of the tablet: 102.5 mg) and 5 mg of levocetirizine (total weight of the tablet: 103 mg). The rate of the composition charged in the capsule body to the volume thereof was satisfactorily about 0.76 g/mL.

Example 5

Preparation of Composite Formulation V

| Aceclofenac Layer | |
| --- | --- |
| Aceclofenac | 100.0 mg |
| Lactose | 11.0 mg |
| Microcrystalline Cellulose | 30.0 mg |
| Sodium Starch Glycolate | 7.5 mg |
| Magnesium Stearate | 1.5 mg |
| Opadry ® Y-1-7000 | 3.0 mg |
| Distilled Water | (15.0 mg) |
| Eperisone Layer | |
| Eperison Hydrochloride | 50.0 mg |
| Lactose | 10.0 mg |
| Corn Starch | 7.5 mg |
| Microcrystalline Cellulose | 10.0 mg |
| Polyvinylpyrrolidone K-30 | 4.0 mg |
| Magnesium Stearate | 1.5 mg |
| Opadry ® Y-1-7000 | 2.0 mg |
| Distilled Water | (10.0 mg) |

An aceclofenac tablet was prepared by mixing the ingredients listed above for the aceclofenac layer and pressing the resulting mixture into a tablet using a tablet press machine, wherein the diameter of the dye was 4.5 mm, the radius of the curvature of the lower punch was 3.0 mm, and the upper punch was flat, followed by coating the resulting tablet with a coating solution prepared by dissolving Opadry® Y-1-7000 in distilled water.

Meanwhile, the ingredients listed above for the eperisone layer were admixed. Then, an eperisone tablet was prepared by using the same tablet press machine as that used for preparing the aceclofenac tablet to press the mixture into a tablet, followed by coating the resulting tablet with a coating solution prepared by dissolving Opadry® Y-1-7000 in distilled water.

The two tablets were charged in the capsule body of a No. 3 hard capsule (vol. of body: 0.27 mL). The aceclofenac tablet was first charged in the capsule body with its curved-end facing down, and the eperisone tablet was then charged therein with its curved-end facing up. Subsequently, the capsule body was closed with a capsule cap to produce a composite formulation comprising 100 mg of aceclofenac (total weight of the tablet: 153.0 mg) and 50 mg of eperisone hydrochloride (total weight of the tablet: 85 mg). The rate of the composition charged in the capsule body to the volume thereof was satisfactorily about 0.88 g/mL.

Comparative Example 1

Preparation of Composite Formulation VI

Commercially available a 50 mg Cozaar tablet (MSD, losartan potassium 50 mg) and a Norvasc tablet (Pfizer, amlodipine 5 mg) were charged in a hard capsule to yield a composite formulation. The weight of the 50 mg Cozaar tablet and the Norvasc tablet were about 154 mg and about 200 mg, respectively. The smallest possible size of a hard capsule capable of accommodate said two tablets was No. 0 (vol. of body: 0.68 mL). The charge rate of the composite formulation of the 50 mg losartan tablet and the 5 mg Norvasc tablet was 0.52 g/mL.

Comparative Example 2

Aspirin Single Formulation

The charge rate of a commercially available aspirin capsule formulation, Astrix® capsule (Boryung Pharmaceuticals, Korea; aspirin 100 mg), was analyzed. Astrix was charged in a No. 4 capsule (vol. of body: 0.20 mL), wherein the total weight of the content charged in the capsule was about 116 mg, indicating a charge rate of 0.58 g/mL.

Comparative Example 3

Pregabalin Single-Drug

The charge rate of a commercially available pregabalin capsule formulation, Lyrica® capsule (Pfizer, pregabalin 150 mg), was analyzed. Lyrica was charged in a No. 2 capsule, wherein the total weight of the content charged in the capsule was about 200 mg, indicating a charge rate of 0.54 g/mL.

Experimental Example 1

Porosity Measurement

The porosity in a hard capsule composite formulation was measured as summarized below. Microcrystalline cellulose having no difference between its bulk density and tapped density (Cellets 100, PHARMATRANS; density=0.80 g/cm$^3$) was used to measure the mass of microcrystalline cellulose required to fill in a vacant hard capsule with its body closed with a cap, which mass was converted to volume (Vb). Subsequently, the mass of microcrystalline cellulose required to fill in the hard capsule was measured while tablets were also charged therein, which mass was converted to volume (Vp). The porosity was calculated by the formula below.

$$\text{Percent porosity}(P,\%) = [(Vb - Vp)/Vb)] \times 100 = [1 - Vp/Vb)] \times 100$$

The porosities of composite formulations of Examples 1 to 5 and Comparative Examples 1 to 3 were measured and summarized in Table 1.

TABLE 1

| Examples | Cap. Sz. | Mass of content (g) | Charge Rate (g/mL) | Porosity (%)* |
| --- | --- | --- | --- | --- |
| Ex. 1 | No. 2 | 0.306 | 0.83 | 9.1% |
| Ex. 2 | No. 2 | 0.306 | 0.83 | 11.2% |
| Ex. 3 | No. 3 | 0.283 | 0.76 | 14.5% |
| Ex. 4 | No. 3 | 0.206 | 0.76 | 15.3% |
| Ex. 5 | No. 3 | 0.238 | 0.88 | 6.7% |
| Co. Ex. 1 | No. 0 | 0.354 | 0.52 | 49.2% |
| Co. Ex. 2 | No. 4 | 0.116 | 0.58 | 32.5% |
| Co. Ex. 3 | No. 2 | 0.200 | 0.54 | 25.9% |

*Porosity was calculated with the mass of microcrystalline cellulose.

As shown in Table 1 above, Examples 1 to 5 demonstrated satisfactory charge rates of 0.7 g/mL or greater and porosities of 20% or less. In contrast, Comparative Examples 1 to 3 indicated unsatisfactory charge rates of 0.6 or less and porosities of 25% or greater.

Experimental Example 2

Stability Test Under Accelerated Conditions

The dual composite formulation of losartan and amlodipine of Example 1 and the triple composite formulation of losartan, amlodipine and hydrochlorothiazide of Example 2 were stored under accelerated conditions according to the following conditions. The amount of degradation products of each active ingredient was measured to compare the stability of the composite formulations. The results are shown in Table 4.

<Accelerated Storage Conditions>

Storage conditions: contained in an HDPE bottle @ 40° C., 75% RH

Test duration: initial, 1 and 2 months

Analysis target: losartan potassium, amlodipine and hydrochlorothiazide

<Analysis Conditions of Losartan and Amlodipine>

Column: stainless column (internal diameter of about 4.6 mm and length of 5 cm) packed with octadecylsilyl silica gel for liquid chromatography (e.g., Symmetry C18)

Mobile phase (Eluent): A—6 nM sodium hexanesulfonate monohydrate added with 0.05% phosphoric acid; B—methanol Gradient system

TABLE 2

| Time (min) | Eluent A (%) | Eluent B (%) |
|---|---|---|
| 0 | 56 | 44 |
| 5 | 56 | 44 |
| 13 | 20 | 80 |
| 13.1 | 56 | 44 |
| 15 | 56 | 44 |

Detector: UV-absorption detector (absorbance at 239 nm)

Flow rate: 1.5 mL/min

Injection volume: 10 μL

Column temperature: 45° C.

<Analysis Conditions of Hydrochlorothiazide>

Column: stainless column (internal diameter of about 4.6 mm and length of 5 cm) packed with octadecylsilyl silica gel for liquid chromatography (e.g., Symmetry C18)

Mobile phase (Eluent): A—acetonitrile:methanol=3:1 (v/v); B—formic acid:water=5:995 (v/v)

Gradient system

TABLE 3

| Time (min) | Eluent A (%) | Eluent B (%) |
|---|---|---|
| 0 | 3 | 97 |
| 5 | 3 | 97 |
| 14 | 36 | 64 |
| 20 | 90 | 10 |
| 25 | 3 | 97 |
| 28 | 3 | 97 |

Detector: UV-absorption detector (absorbance at 275 nm)

Flow rate: 1.0 mL/min

Injection volume: 10 μL

Column temperature: 35° C.

TABLE 4

Changes in Content of Losartan, Amlodipine and Hydrochlorothiazide

| Ingredient | Example | Initial | 1 Month | 2 Months |
|---|---|---|---|---|
| Amlodipine | Ex. 1 | 100.0% | 99.8% | 99.7% |
|  | Ex. 2 | 100.0% | 99.5% | 99.4% |
| Losartan | Ex. 1 | 100.0% | 99.7% | 99.6% |
|  | Ex. 2 | 100.0% | 99.6% | 99.5% |
| Hydrochlorothiazide | Ex. 1 | — | — | — |
|  | Ex. 2 | 100.0% | 99.6% | 99.5% |

As shown in Table 4 above, the duel composite formulation of losartan and amlodipine of Example 1 and the triple composite formulation of losartan, amlodipine and hydrochlorothiazide of Example 2 showed insignificant changes in the content of losartan, amlodipine and hydrochlorothiazide, indicating exceptionally good storage stability.

What is claimed is:

1. A composite hard capsule adapted for oral administration of a physiologically active substance, said hard capsule comprising
a capsule having a hemispherical closure at each end and an internal space; and
one or more tablets placed in the capsule,
wherein the tablets as a whole have a shape conforming to the internal space of the capsule; the charge rate of the capsule is 0.6 g/mL to 1.0 g/mL; and the porosity of the interior of the capsule is 20% or less, being an empty space not occupied by the tablet.

2. The composite hard capsule of claim 1, wherein the tablets consist of a first tablet and a second tablet;
wherein the first tablet and the second tablet each have a cylindrical body with a hemispherical end and a flat end; and
wherein the tablets are positioned in the capsule with their flat ends facing each other.

3. The composite hard capsule of claim 2, wherein each tablet is coated.

4. The composite hard capsule of claim 1, wherein the tablets consist of a first tablet, a second tablet, and a third tablet;
wherein the first tablet and the second tablet each have a cylindrical body with a hemispherical end and a flat ends;
wherein the third tablet has a cylindrical body with two flat ends; and
wherein the third tablet is positioned between the first tablet and the second tablet in the capsule with their flat ends facing one another.

5. The composite hard capsule of claim 4, wherein each tablet is coated.

6. The composite hard capsule of claim 1, wherein the ratio of the radius of the hemispherical ends of the capsule to the radius of the hemispherical ends of the tablet is 1:0.8 to 1:0.99.

7. The composite hard capsule of claim 1, wherein each tablet has embossed or engraved stripes in horizontal, vertical, or spiral pattern.

8. The composite hard capsule of claim 1, wherein each tablet comprises the physiologically active substance and pharmaceutically acceptable additives.

9. The composite hard capsule of claim 8, wherein the additives are selected from the group consisting of pharmaceutically acceptable diluents, disintegrants, binders, stabilizers and lubricants.

10. The composite hard capsule of claim 8, wherein the capsule contains two or three tablets, and wherein the physiologically active substance contained in one of the tablets is different from the physiologically active substance contained in the other tablets.

11. The composite hard capsule of claim 1, wherein each tablet is coated.

* * * * *